United States Patent [19]
Fujiwara et al.

[11] Patent Number: 5,085,993
[45] Date of Patent: Feb. 4, 1992

[54] **COENZYME-INDEPENDENT L-SORBOSONE DEHYDROGENASE FROM *PSEUDOMONAS PUTIDA***

[75] Inventors: Akiko Fujiwara; Tatsuo Hoshino, both of Kamakura, Japan

[73] Assignee: Hoffmann-La Roche Inc., Nutley, N.J.

[21] Appl. No.: 283,706

[22] Filed: Dec. 13, 1988

[30] Foreign Application Priority Data

Dec. 24, 1987 [EP] European Pat. Off. ........ 87119187.0

[51] Int. Cl.$^5$ .......................... C12P 7/60; C12N 9/02; C12N 1/00
[52] U.S. Cl. .................................. 435/138; 435/189; 435/877
[58] Field of Search .................. 435/138, 189, 877

[56] References Cited

U.S. PATENT DOCUMENTS 3,043,749  7/1962  Huang ............................... 435/877
3,907,639  9/1975  Makover et al. .................. 435/877
4,902,617  2/1990  Fujiwara et al. .................. 435/138

OTHER PUBLICATIONS

Kitamura et al., "Metabolism of L-Sorbose by Enzymes from *Gluconobacter melanogenus* IFO 32 93", Eur. J. Appl. Microbiol., vol. 2, pp. 1–7, 1975.

Makover et al., "New Mechanisms for the Biosynthesis and Metabolisms of 2-Keto-L-Gulonic Acid in Bacteria", Biotech. Bioeng., vol. 17, No. 10, pp. 1485–1514, 1975.

*Primary Examiner*—David M. Naff
*Assistant Examiner*—Jon P. Weber
*Attorney, Agent, or Firm*—George M. Gould; William H. Epstein

[57] ABSTRACT

A coenzyme-independent L-sorbosone dehydrogenase has been prepared from a microorganism belong to the genus Pseudomonas, which acts on L-sorbosone to produce 2-keto-L-gulonic acid. The enzyme is membrane bound and has a molecular weight of about 47,000 kDa. The enzyme is used to carry out the conversion of L-sorbosone to 2-keto-L-gulonic acid.

6 Claims, No Drawings

COENZYME-INDEPENDENT L-SORBOSONE DEHYDROGENASE FROM *PSEUDOMONAS PUTIDA*

BACKGROUND OF INVENTION

The compound 2-KGA(2-keto-L-gulonic acid) is an important precursor for Vitamin C. Reactions to convert L-sorbosone to 2-KGA are known. In fact 2-KGA production from L-sorbosone using cell free extracts of microorganisms was reported in several prior publications. In U.S. Pat. No. 3,907,639, microorganisms belonging to the genus Acetobacter, Pseudomonas, Escherichia, Serratia, Bacillus, Staphylococcus, Aerobacter, Alcaligenes, Penicillium, Candida and Gluconobacter were reported to be capable of such a conversion. Furthermore, Kitamura et al., Europ. J. Appl. Microbiol., 2.1, (1975) reported that the L-sorbosone oxidizing enzyme found in Gluconobacter melanogenes IFO3293 required neither coenzyme nor an electron acceptor for the development of enzyme activity. Makover et al., Biotechnol. Bioeng. 17, 1485, (1975) reported the presence of L-sorbosone dehydrogenase activity in the particulate fraction of Pseudomonas putida ATCC 21812. However, the L-sorbosone dehydrogenase has never been isolated from Pseudomonas putida in the form of a homogeneous protein. Therefore, the physico-chemical properties of the enzyme have not been specified yet.

SUMMARY OF THE INVENTION

This invention is directed to producing the enzyme L-sorbosone dehydrogenase as a homogenous protein. The homogenous protein is an enzyme having activity capable of converting L-sorbosone to 2-KGA in the presence of an electron acceptor without the need for a coenzyme.

The present invention relates to a novel enzyme having coenzyme independent L-sorbosone dehydrogenase activity and a process for producing this enzyme. It has been found that the purified enzyme isolated from a membrane fraction of cells of specific microorganisms catalyzes the oxidation of L-sorbosone to 2-KGA. The present invention has been accomplished on the basis of this finding.

It is an object of the present invention to provide to novel enzyme having coenzyme independent L-sorbosone dehydrogenase activity to convert L-sorbosone to 2-KGA. It is another object to provide a process for producing this novel L-sorbosone dehydrogenase by cultivation of a microorganisms belonging to the genus Pseudomonas or a mutant thereof which are capable of producing the novel L-sorbosone dehydrogenase in the cells, and isolating said enzyme in pure form from said cells. This isolation can be accomplished by disruption of the cells, and isolation and purification of the enzyme from the cell free extract of disrupted cells, preferably from the membrane fraction of microorganisms.

DETAILED DESCRIPTION

In accordance with this invention, the enzyme L-sorbosone dehydrogenase is produced as a homogenous protein. The enzyme L-sorbosone dehydrogenase, is a protein which has activity capable of converting L-sorbosone to 2-KGA in the presence of an electron acceptor without the need for a coenzyme.

A coenzyme may be employed in connection with the L-sorbosone dehydrogenase protein to convert L-sorbosone to 2-KGA. However, the presence of such a coenzyme is not necessity for carrying out the aforementioned conversion. Its presence may only enhance the activity of the enzyme.

In carrying out the conversion from L-sorbosone to 2-KGA, this reaction generally carried out in the presence of an electron acceptor. Any conventional electron acceptors such as those mentioned hereinafter can be utilized for carrying out this conversion. The electron acceptors mentioned hereinafter are the most preferred for use in this conversion.

The L-sorbosone dehydrogenase that is produced in accordance with this invention consists of a single homogeneous subunit having a molecular weight of $47,000 \pm 5,000$ as measured by sodium dodecylsulfate polyacrylamide gel electrophoresis. The L-sorbosone dehydrogenase activity of the enzyme of this invention is enhanced by addition of pyrroloquinoline quinone and decreased by the presence of $Cu^{2+}$ or $Mn^{2+}$ ions. The enzyme of this invention exhibits the activity of being capable of converting L-sorbosone to 2-KGA most optimally at a pH of about 7 to 8, and provides high initial reaction rates in said conversion reaction at a temperature of from about 20° C. to about 40° C. However, in case where the incubation would be carried out for a long period of time at 30° C. or higher, the enzyme is decomposed.

In accordance with this invention, the enzyme is produced through the isolation from a cultivation product produced by a microorganism belonging to the class Pseudomonas by cultivating cells of this microorganism in a suitable medium and isolating the enzyme thus produced from these cells. Any such microorganism capable of converting L-sorbosone to 2-KGA can be utilized for this purpose with Pseudomonas putida being preferred. In accordance with this invention, any Pseudomonas microorganism capable of producing this enzyme can be utilized to produce the product from which the enzyme of this invention can be isolated in pure or homogenous form. In accordance with this invention, any nutrient medium capable of growing said microorganism can be utilized as the culture medium for producing the enzyme product from which the enzyme can be isolated in pure or homogeneous form.

The physico-chemical properties of the purified sample of the novel coenzyme independent L-sorbosone dehydrogenase prepared by Examples set forth later on are as follows:

1) Enzyme activity

L-Sorbosone dehydrogenase, i.e. the enzyme of the present invention catalyzes the oxidation of L-sorbosone to 2-KGA in the presence of an electron acceptor according to the following reaction formula:

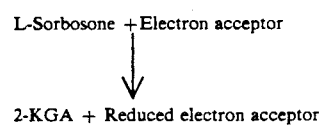

The enzyme does not utilize oxygen as an electron acceptor. However, any conventional compound which has the ability to act as an electron acceptor can be utilized in conjunction with the enzyme of this invention to oxidize L-sorbosone to 2-KGA. As an electron acceptor, 2,6-dichlorophenolindophenol (hereinafter referred to as DCIP), phenazine methosulphate, Wurster's blue, ferricyanide, coenzyme Q or cytochrome C, etc. can be used.

ASSAY OF ENZYME ACTIVITY

Enzyme assay was carried out at 25° C. by measuring the decrease of absorbance at 600 nm of DCIP spectrophotometrically. One unit of enzyme activity was defined as the amount of enzyme which catalyzed the reduction of 1 μmole of DCIP per minute. The extinction coefficient of DCIP at pH 7.0 was taken as 9.45 $mM^{-1}$.

The basal reaction mixture was prepared by mixing 6 ml of 0.1M potassium phosphate buffer (pH 7.0) containing 0.3% Triton X-100, 0.45 ml of 2.5 mM DCIP and 10.35 ml of water. A cuvette with 1 cm light path contained 0.4 ml of basal reaction mixture, 20 μl of 10 mM phenazine methosulfate, 10 μl of enzyme solution and 20 μl of 110 mM L-sorbosone solution. A reference cuvette contained all the reagents except enzyme solution, but 10 μl of water was added instead. The reaction was started by the addition of the substrate.

2) Substrate specificity

Substrate specificity of the enzyme was determined using the same enzyme assay method as described in the above 1) except that 20 μl of each of the various substrate solutions (100 mM) was used instead of L-sorbosone. The results of the measurement are shown in Table 1. It was revealed that the enzyme of the present invention acts on a variety of aldehyde compounds.

TABLE 1

Substrate specificity of coenzyme independent L-sorbosone dehydrogenase from *P. putida* ATCC 21812

| Substrate | Relative activity (%) |
|---|---|
| L-Sorbosone | 100.0 |
| Methylglyoxal | 288.9 |
| Glyoxal | 172.2 |
| Glutaraldehyde | 147.2 |
| Glyceraldehyde | 88.9 |
| Glycolaldehyde | 83.3 |
| Propionaldehyde | 61.1 |
| Glyoxilic acid | 52.8 |
| Benzaldehyde | 27.8 |
| Acetaldehyde | 22.2 |
| L-Idose | 19.4 |
| D-Mannose | 0 |
| D-Fructose | 0 |
| D-Glucose | 0 |
| L-Sorbose | 0 |

3) Optimum pH

The correlation between the reaction rate of the L-sorbosone dehydrogenase and pH was determined in potassium phosphate and Tris-HCl buffers. The result is shown in Table 2. The enzyme showed the highest enzyme activity at pH range between 7.0 and 8.0.

TABLE 2

Optimum pH of coenzyme independent L-sorbosone dehydrogenase of *P. putida* ATCC 21812

| pH | Buffer (0.1M) | Relative activity (%) |
|---|---|---|
| 6.0 | Potassium phosphate | 44.4 |
| 6.5 | " | 77.8 |
| 7.0 | " | 100.0 |
| 7.5 | " | 114.0 |
| 8.0 | " | 100.0 |
| 8.0 | Tris-HCl | 100.0 |
| 8.5 | " | 80.6 |

The purified enzyme was added to the buffers of various pH's for 24 hours at 4° C. The residual activity was assayed under the standard assay conditions as described in the above 1). The results of the measurement are shown in Table 3. The purified enzyme was relatively stable in alkaline pH and became unstable with the increase of acidity.

TABLE 3 pH stability of coenzyme independent L-sorbosone dehydrogenase of *P. putida* ATCC 21812*

| pH | Buffer | Relative activity (%) |
|---|---|---|
| 4.0 | Acetate | 36.8 |
| 4.5 | " | 36.8 |
| 5.0 | " | 57.9 |
| 5.5 | " | 81.6 |
| 6.0 | " | 78.9 |
| 6.0 | Potassium phosphate | 68.4 |
| 6.5 | " | 73.7 |
| 7.0 | " | 100.0 |
| 7.5 | " | 94.7 |
| 8.0 | " | 105.3 |
| 8.0 | Tris-HCl | 89.5 |
| 8.5 | " | 94.7 |

*The purified enzyme was kept at indicated pH for 24 hours at 4° C. and the remaining activity was measured at pH 7.0.

5) Heat stability

The purified enzyme was treated for 10 minutes at various temperatures in 10 mM potassium phosphate buffer (pH 7.0), and then immediately cooled in iced water.

The residual activity was measured under the standard assay conditions as described under 1) above. The results are shown in Table 4. This enzyme was unstable and lost about one half of its activity by the treatment at 30° C. for 10 minutes.

TABLE 4

Thermostability of coenzyme independent L-sorbosone dehydrogenase of *P. putida* ATCC 21812*

| Temperature (°C.) | Relative activity (%) |
|---|---|
| 4 | 100.0 |
| 20 | 82.9 |
| 30 | 54.3 |
| 40 | 40.0 |
| 50 | 11.4 |
| 60 | 8.6 |

*The purified enzyxe was treated at indicated temperature for 10 minutes, and the remaining activity was measured at pH 7.0.

6) Optimum temperature

The enzymatic activities of L-sorbosone dehydrogenase were measured at temperatures from 10° C. to 40° C. in the reaction system as described under 1) above. The results are shown in Table 5. This enzyme showed its optimum temperature between 20° C. and 40° C.

TABLE 5

Optimum temperature of coenzyme independent L-sorbosone dehydrogenase from *P. putida* ATCC 21812*

| Temperature (°C.) | Relative activity (%) |
|---|---|
| 10 | 58.8 |
| 15 | 76.5 |
| 20 | 103.0 |
| 25 | 100 |
| 30 | 100 |
| 35 | 111.8 |
| 40 | 105.9 |

*In the Table, the initial reaction rate of the enzyme was compared at the temperatures listed. Thus the optimum temperature has to be viewed with the initial reaction rate.

7) Molecular weight

The purified enzyme with specific activity of 51.5 unit/mg protein was treated by sodium dodecyl sulfate (SDS) and was analyzed for its molecular weight of the subunit by SDS-polyacrylamide gel electrophoresis. It was proved that the enzyme consists of a single homogeneous subunit with a molecular weight of 47,000±5,000.

8) Measurement of the Km value

In the procedure described under 1) above, the velocities of oxidizing reactions with varying concentrations of L-sorbosone were measured to determine the apparent Michaelis constant (Km) for L-sorbosone. Km value was calculated to be 13±2 mM with DCIP and phenazine methosulfate as electron acceptors.

9) Effect of metal ions

Using the assay procedure described under 1) above, the effect of various metal ions on the enzyme activity was examined. The results of the measurement are shown in Table 6. $Cu^{2+}$ and $Mn^{2+}$ strongly inhibited the enzyme.

TABLE 6

Effect of metal ions on coenzyme independent L-sorbosone dehydrogenase of P. putida ATCC 21812

| Metal ion | Concentration (mM) | Relative activity (%) |
| --- | --- | --- |
| None | 0 | 100.0 |
| $Cu^{2+}$ | 0.8 | 0 |
| $Mn^{2+}$ | 0.8 | 0 |
| $Ni^{2+}$ | 4.0 | 48.9 |
| $Zn^{2+}$ | 2.0 | 48.9 |
| $Co^{2+}$ | 0.8 | 57.8 |
| $Fe^{3+}$ | 0.8 | 68.9 |
| $Mo^{6+}$ | 0.8 | 77.8 |
| $Mg^{2+}$ | 4.0 | 100.0 |

10) Effect of inhibitors

Using the assay procedure described under 1) above, the effect of inhibitors on the enzyme activity was examined. The results are shown in Table 7. Sodium azide and monoiodoacetate slightly inhibited the enzyme activity.

TABLE 7

Effect of inhibitors on coenzyme independent L-sorbosone dehydrogenase of P. putida ATCC 21812

| Inhibitors | Concentration (mM) | Relative activity (%) |
| --- | --- | --- |
| None | 0 | 100.0 |
| $NaN_3$ | 25.0 | 77.3 |
| $ICH_2COOH$ | 5.0 | 88.6 |

11) Prosthetic group

The absorption spectrum of the purified enzyme showed a peak at about 350 nm and a wide shoulder at 380–420 nm in the visible region. These absorption maxima were the characteristic of quinoprotein enzyme which had pyrroloquinoline quinone (hereinafter referred to as PQQ) as a prosthetic group.

12) Effect of addition of PQQ on the enzyme activity

Using the assay procedure described under 1) above, the effect of addition of PQQ on the enzyme activity was examined. The results are shown in Table 8. Significant increase of the enzyme activity was observed by the addition of PQQ.

TABLE 8

Effect of PQQ on the activity of coenzyme independent L-sorbosone dehydrogenase of P. putida ATCC 21812

| PQQ concentration (Micro Moles) | Relative enzyme activity |
| --- | --- |
| 0 | 100 |
| 0.1 | 106 |
| 0.2 | 142 |
| 0.5 | 150 |
| 0.9 | 158 |
| 6.0 | 174 |
| 15.0 | 192 |

13) Purification method

Purification of coenzyme independent L-sorbosone dehydrogenase may be effected by known purification methods and by a combination of known purification methods respectively, such as ion exchange chromatography, absorption chromatography, gel-filtration, gel-electrophoresis, salting out and dialysis.

The coenzyme independent L-sorbosone dehydrogenase provided by the present invention can be prepared by cultivating an appropriate microorganism, disrupting the cells and isolating and purifying it from cell free extract of disrupted cells, preferably from the membrane fraction of microorganism.

The microorganisms used for the present invention are microorganisms belonging to genus Pseudomonas or mutants thereof, preferably Pseudomonas putida.

Microorganisms belonging to the genus Pseudomonas which are used in the present inventions can be isolated from natural sources or available from the culture collections. The mutants derived thereof may also be used according to the present invention.

The mutants used in the present invention can be obtained by treating a wild type strain with a mutagen such as ultraviolet irradiation, X-ray irradiation, γ-ray irradiation or through contact with a nitrous acid or other suitable mutagens, or by isolating a clone occurring by spontaneous mutation. These mutations of a wild type strain or a mutant strain thereof may be effected in any of the ways well know per se for the particular purpose by one skilled in the art. Many of these methods have been described in various publications, for example, "Chemical Mutagens" edited by Y. Tajima, T. Yoshida and T. Kada, published by Kodansha Scientific Inc., Tokyo, Japan, in 1973.

Examples of the strains most preferably used in the present invention are Pseudomonas putida ATCC 21812 and the like. Pseudomonas putida ATCC 21812 is available from American Type Culture Collection (12301 Parklawn Drive, Rockville, Maryland 20852, U.S.A.).

The microorganism may be cultured in an aqueous medium supplemented with appropriate nutrients under aerobic condition. The cultivation may be conducted at pH of 4.0 to about 8.0, preferably from 5.5 to 7.5. A cultivation period varies depending upon the nutrient medium, preferably about 10 to 100 hours. A preferred temperature range for carrying out for the cultivation is from about 10° C. to 40° C., preferably from 25° C. to 35° C.

It is usually required that the culture medium contains nutrients, e.g. assimilable carbon sources such as glycerol, D-mannitol, D-sorbitol, erythritol, ribitol, xylitol, arabitol, inositol, dulcitol, D-ribose, D-fructose, D-frucose, D-glucose, gluconate, maltose and sucrose, preferably D-sorbitol or glycerol; digestible nitrogen sources such as organic substances, for example, peptone, yeast extract, soybean meal and corn steep liquor and inorganic substances, for example, ammonium sulfate, ammonium chloride and potassium nitrite; vitamins and trace elements.

In the following, an embodiment for isolation and purification of L-sorbosone dehydrogenase from the microorganisms after the cultivation is briefly described.

(1) Cells are harvested from the fermentation broth by centrifugation.
(2) The cells are suspended in the buffer solution and disrupted by means of a homogenizer, sonicator or treatment with lysozyme and the like to give a disrupted solution of cells.
(3) L-sorbosone dehydrogenase is isolated and purified from cell free extract of disrupted cells, preferably from the membrane fraction of microorganisms.

The L-sorbosone dehydrogenase provided by the present invention is useful as a catalyst for the production of 2-KGA from L-sorbosone. The reaction should be conducted at pH values of from about 5.0 to about 10.0 in the presence of an electron acceptor, for example, DCIP, phenazine methosulfate, Wurster's blue, ferricyanide, coenzyme Q, cytochrome C and the like in a solvent such as phosphate buffer, tris-HCl buffer and the like. A preferred temperature range for carrying out the reaction is from about 10° C. to about 50° C. When the pH and temperature are set at about 7.0–8.0 and 30° C., respectively, reaction usually brings about most preferable results.

Concentration of L-sorbosone in a solvent varies depending on other reaction conditions but, in general, is desirable to be about 10–100 g/L, most preferably from about 30–40 g/L.

In the reaction, the enzyme may also be used in an immobilized state with an appropriate carrier. Any means of immobilizing enzyme generally known to the art may be used. For instance, the enzyme may be bound directly to a membrane, granules or the like of a resin having functional group(s), or it may be bound through bridging compounds having bifunctional group(s), for example, glutaraldehyde, to the resin.

The following examples illustrate the present invention:

EXAMPLE 1

Preparation of L-sorbosone dehydrogenase

1) Cultivation of P. putida ATCC 21812

The agar slant culture of P. putida was inoculated into 5 ml of the medium composed of 70 g/L of glycerol, 15 g/L of yeast extract (Oriental Co., Ltd.) and 2.5 g/L of $MgSO_4 \cdot 7H_2O$ in a test tube, and incubated at 30° C. for 2 days on a tube shaker (280 r.p.m.). Two ml of this culture was transferred to 100 ml of the same medium in a 500 ml-Erlenmeyer flask, and cultivated at 30° C. for 20 hours on a rotary shaker (180 r.p.m.). The culture (400 ml) thus prepared was used as an inoculum for a 30L-jar fermentor containing 20L of the same medium. The jar fermentor was operated at 30° C., 250 r.p.m. for agitation and 20L/min. for aeration. After 40 hours fermentation, the culture was harvested to collect the cells by centrifugation (8,000 r.p.m., 10,000 g). From 20L of broth, 920 g (wet weight) of the cells was obtained. The cells were frozen at −20° C. until use.

2) Preparation of membrane fraction

The frozen cells of P. putida (760 g, wet weight) were thawed and suspended in 3,800 ml of 0.85% NaCl solution. The cell suspension was then homogenized by a Dyno Mill homogenizer (Willy A. Bachofen Co., Basle) in the presence of glass beads (0.1 mm in diameter) at 2,000 r.p.m. for 4 minutes at 4° C.

The homogenate thus prepared was centrifuged at $1,800 \times g$ for 10 minutes to remove the cell debris and glass beads. The resulting supernatant was centrifuged at $80,000 \times g$ for 60 minutes, and then the precipitate was collected as membrane fraction (266 g).

3) Solubilization of L-sorbosone dehydrogenase from membrane fraction

The membrane fraction (266 g, wet weight) was suspended in 1,100 ml of 50 mM potassium phosphate buffer, pH 7.0, containing 1% Triton X-100, stirred for 15 hours and centrifuged at $80,000 \times g$ for 1 hour to obtain the supernatant. The supernatant (1,000 ml) thus obtained was dialyzed against 20L of 10 mM potassium phosphate buffer, pH 7.0, containing 0.1% Triton X-100 for 15 hours and used for DEAE-Sepharose CL-6B (Pharmacia Fine Chemicals) column chromatography.

4) DEAE-Sepharose CL-6B column chromatography (I)

The dialyzed supernatant was applied to a DEAE-Sepharose CL-6B column ($3.8\phi \times 30$ cm), which had been equilibrated with the same buffer described under 3) above. The column was washed with the same buffer, and the enzyme was eluted by a linear gradient of NaCl to 0.5M.

5) DEAE-Sepharose CL-6B column chromatography (II)

The active fractions from the previous step were combined and dialyzed against the same buffer described under 3) above for 15 hours, and then applied to a DEAE-Sepharose (diethylaminoethyl-agarose) CL-6B column ($2.5\phi \times 25$ cm) equilibrated with the same buffer. The column was washed with the same buffer, and the enzyme was eluted by a linear gradient of NaCl to 0.3M.

6) DEAE(diethylaminoethyl-polyvinyl-type)-Toyopearl 650s (Toyo Soda) column chromatography The active fractions from the previous step were combined and dialyzed against the same buffer described under 3) above for 15 hours, and then applied to a DEAE-Toyopearl 650s column ($2.0\phi \times 20$ cm) equilibrated with the same buffer. The column was washed with the same buffer, and then the enzyme was eluted by a linear gradient of NaCl to 0.1M.

7) Hydroxyapatite HCA 100S (Mitsui Toatsu) column chromatography

The active fractions from the previous step were combined and dialyzed against 1 mM potassium phosphate buffer (pH 7.0) containing 0.1% Triton X-100 for 15 hours, and then applied to a hydroxyapatite HCA 100S column ($2.0\phi \times 10$ cm) equilibrated with the same buffer. The enzyme was eluted with the same buffer.

8) TSK-GEL(polyvinyl type) Toyopearl HW 60S (Toyo Soda) column chromatography I and II The active fractions from the previous step were combined and concentrated by ultrafiltration using the membrane filter (Diaflo PM-30, Amicon; polysulfone type; fractionation size: MG ~30000) to a small volume (ca. 2 ml). Then, the concentrate was applied to the column packed with TSK-GEL Toyopearl HW 60S (1.5 cm$\phi \times 80$ cm) in 10 mM potassium phosphate buffer, pH 7.0, containing 0.1% Triton X-100. The column was developed by the same buffer. The active fractions were combined, concentrated and rechromatographed on the same column.

Summary of the purification procedure of L-sorbosone dehydrogenase is shown in Table 9.

9) Electrophoretic analysis

The purified enzyme with specific activity of 51.5 unit/mg protein was treated by sodium dodecyl sulfate (SDS) and was analyzed for its purity by SDS-polyacrylamide electrophoresis. It was proved that the enzyme consists of a single homogeneous subunit with a molecular weight of 47,000±5000.

10) Identification of the reaction product

The reaction mixture containing 0.4 ml of the purified enzyme solution, 0.05 ml of 0.5M potassium phosphate buffer (pH 7.0), 0.05 ml of 0.5M L-sorbosone and 0.02 ml of 0.2M phenazine methosulfate was incubated at 30° C. for 60 minutes. The reaction product was analyzed by thin layer chromatography and high performance liquid chromatography. As a result, the product was identified to be 2-keto-L-gulonic acid in comparison with an authentic sample.

TABLE 9

Purification of L-sorbosone dehydrogenase from *Pseudomonas putida*

| Fraction | Total protein (mg) | Total activity (unit) | Specific activity (unit/mg protein) | Yield (%) |
| --- | --- | --- | --- | --- |
| Solubilized fraction | 6,900 | 204.25 | 0.03 | 100 |
| DEAE-Sepharose CL-6B (I) | 1,870 | 134.86 | 0.07 | 68 |
| DEAE-Sepharose CL-6B (II) | 536.3 | 75.68 | 0.14 | 37 |
| DEAE-Toyopearl 650S | 48.3 | 48.71 | 1.01 | 24 |
| Hydroxyapatite HCA 100S | 2.3 | 31.85 | 13.85 | 16 |
| TSK GEL Toyopearl HW60S (I) | 0.9 | 30.76 | 34.18 | 15 |
| TSK GEL Toyopearl HW60S (II) | 0.4 | 20.60 | 51.5 | 10 |

EXAMPLE 2

The reaction mixture containing 5 ml of purified coenzyme independent L-sorbosone dehydrogenase (total activity, 206 unit), as prepared by the manner as described in the steps (1) to (8) of the Example 1, 1 ml of 0.5M potassium phosphate buffer (pH 7.0), 1 ml of 1M L-sorbosone solution, 0.2 ml of 0.2M phenazine methosulfate solution and 2.8 ml of water were incubated at 25° C. with gentle shaking. As a result, 2-KGA was formed with the rate of 350 mg/hr.

We claim:

1. An enzyme wherein said enzyme is a homogenous protein having the L-sorbosone dehydrogenase activity for converting L-sorbosone to 2-keto-L-gulonic acid in the presence of an electron acceptor without the need for a coenzyme where said protein has a molecular weight of 47,000±5,000 as measured by sodium dodecyl sulfate polyacrylamide gel electrophoresis with said activity of said protein being optimal at a pH of from about 7 to about 8 and at a temperature of from about 20° C. or to about 40° C.

2. The L-sorbosone dehydrogenase enzyme of claim 1 wherein said activity of said protein is enhanced by pyrroloquinoline quinone and decreased by $Cu^{2+}$ or $Mn^{2+}$ ions.

3. The L-sorbosone dehydrogenase enzyme of claim 1 wherein decomposition of said protein occurs at temperatures of 30° C.

4. The L-sorbosone dehydrogenase enzyme of claim 3 wherein said protein is obtained through isolation from a cultivation product produced by a microorganism belonging to the genus Pseudomonas.

5. The L-sorbosone dehydrogenase enzyme of claim 1 wherein said microorganism is *Pseudomonas putida* ATCC 21812.

6. A process for producing 2-KGA comprising oxidizing L-sorbosone in the presence of an enzyme, said enzyme being a homogeneous protein having the L-sorbosone dehydrogenase activity for converting L-sorbosone to 2-Keto-L-gulonic acid in the presence of an electron acceptor without the need for a coenzyme where said protein has a molecular weight of 47,000±5,000 as measured by sodium dodecyl sulfate polyacrylamide gel electrophoresis with said activity of said protein being optimal at a pH of from about 7 to about 8 and at a temperature of from about 20° C. or to about 40° C.

* * * * *

UNITED STATES PATENT AND TRADEMARK OFFICE
CERTIFICATE OF CORRECTION

PATENT NO. : 5,085,993
DATED : FEB. 4, 1992
INVENTOR(S) : FUJIWARA ET AL.

It is certified that error appears in the above-identified patent and that said Letters Patent is hereby corrected as shown below:

Column 10, line 29 before the period should be:

[or a mutant thereof]--.

Signed and Sealed this

Twenty-first Day of September, 1993

Attest:

BRUCE LEHMAN

*Attesting Officer*    *Commissioner of Patents and Trademarks*